United States Patent
Kuusela et al.

(10) Patent No.: US 10,500,417 B2
(45) Date of Patent: Dec. 10, 2019

(54) COMPENSATING FOR LEAKAGE RADIATION IN MLC MODULATED TREATMENT

(71) Applicant: Varian Medical Systems International AG, Cham (CH)

(72) Inventors: Esa Kuusela, Espoo (FI); Juha Kauppinen, Helsinki (FI)

(73) Assignee: Varian Medical Systems International AG, Cham (CH)

( * ) Notice: Subject to any disclaimer, the term of this patent is extended or adjusted under 35 U.S.C. 154(b) by 41 days.

(21) Appl. No.: 15/889,032

(22) Filed: Feb. 5, 2018

(65) Prior Publication Data
US 2019/0240509 A1    Aug. 8, 2019

(51) Int. Cl.
*A61N 5/10*    (2006.01)

(52) U.S. Cl.
CPC .......... *A61N 5/1045* (2013.01); *A61N 5/103* (2013.01); *A61N 5/1049* (2013.01); *A61N 5/1065* (2013.01); *A61N 5/1069* (2013.01); *A61N 5/1081* (2013.01); *A61N 5/1084* (2013.01)

(58) Field of Classification Search
CPC .... A61N 5/103; A61N 5/1045; A61N 5/1049; A61N 5/1065; A61N 5/1069; A61N 5/1081; A61N 5/1084
See application file for complete search history.

(56) References Cited

U.S. PATENT DOCUMENTS

| | | | | |
|---|---|---|---|---|
| 6,473,490 B1* | 10/2002 | Siochi | ..................... | A61N 5/103 378/65 |
| 6,600,810 B1* | 7/2003 | Hughes | ..................... | G21K 1/04 378/147 |
| 2002/0006182 A1* | 1/2002 | Kim | ..................... | A61N 5/1042 378/65 |
| 2003/0086530 A1* | 5/2003 | Otto | ..................... | A61N 5/1042 378/65 |
| 2003/0204336 A1* | 10/2003 | Ritt | ..................... | A61N 5/1048 702/49 |
| 2008/0159478 A1* | 7/2008 | Keall | ..................... | A61N 5/1042 378/65 |
| 2008/0298550 A1* | 12/2008 | Otto | ..................... | A61N 5/103 378/65 |
| 2011/0080990 A1* | 4/2011 | Filiberti | ..................... | A61N 5/1049 378/4 |
| 2012/0256103 A1* | 10/2012 | Luzzara | ..................... | A61N 5/1045 250/492.1 |

(Continued)

*Primary Examiner* — Mark R Gaworecki
(74) *Attorney, Agent, or Firm* — Kilpatrick Townsend & Stockton LLP

(57) ABSTRACT

A treatment planning method and system for determining a treatment plan used to irradiate a treatment volume using a radiation treatment system that includes a multi-leaf collimator (MLC), is disclosed. The treatment plan includes settings for leaf patterns of individual leaves of the MLC, each leaf pattern including a geometry of the individual leaves and forming an aperture for use in the treatment plan. Areas of radiation leakage are identified in each of the leaf patterns, the areas of radiation leakage including first unshielded areas corresponding to gaps that are located between adjacent leaves and outside of the aperture. At least one leakage metric is calculated based on the areas of radiation leakage. A setting for at least one of the leaf patterns can be adjusted based on the at least one leakage metric.

20 Claims, 15 Drawing Sheets

(56) References Cited

U.S. PATENT DOCUMENTS

| | | | |
|---|---|---|---|
| 2017/0084359 A1* | 3/2017 | Constantin | A61N 5/1045 |
| 2017/0143995 A1* | 5/2017 | Bergfjord | A61N 5/1045 |
| 2018/0021596 A1* | 1/2018 | Arai | A61N 5/10 600/1 |
| 2018/0161602 A1* | 6/2018 | Kawrykow | A61B 6/032 |
| 2018/0280733 A1* | 10/2018 | Weidlich | A61B 6/4078 |

* cited by examiner

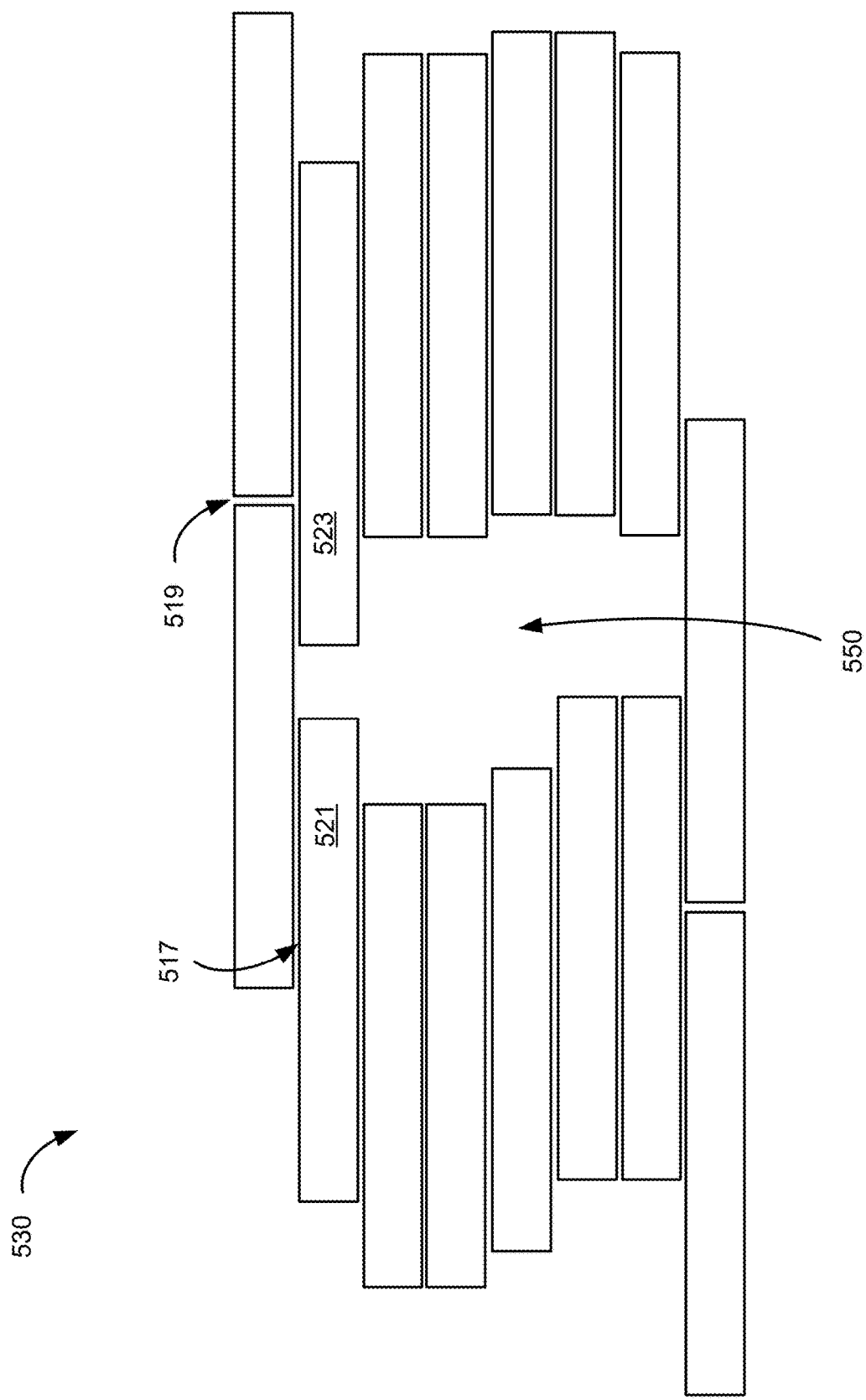

COMPENSATING FOR LEAKAGE RADIATION IN MLC MODULATED TREATMENT

BACKGROUND

Modern radiation therapy techniques include the use of Intensity Modulated Radiotherapy ("IMRT"), typically by means of an external radiation treatment system, such as a linear accelerator, equipped with a multileaf collimator ("MLC"). Use of multileaf collimators in general, and an IMRT field in particular, allows the radiologist to treat a patient from a given direction of incidence to the target while varying the shape and dose of the radiation beam, thereby providing greatly enhanced ability to deliver radiation to a target within a treatment volume while avoiding excess irradiation of nearby healthy tissue. However, it is difficult to take full advantage of this greater freedom afforded by IMRT and other complex radiotherapy techniques, such as volumetric modulated arc therapy (VMAT, where the system gantry moves while radiation is delivered) and three-dimensional conformal radiotherapy ("3D conformal" or "3DCRT").

For example, treatment plans can still provide too much radiation to organs at risk. Some techniques take into consideration the maximum resolution of the MLC based on physical dimensions of the individual leaves. For instance, the width of a leaf limits the precision with which a radiation dose can be delivered through an aperture formed by the leaves. However, conventional techniques fail to take into account the various ways in which leaf geometry contributes to unwanted radiation, i.e., more radiation than desired or radiation delivered to areas that should be left untreated.

BRIEF SUMMARY

In IMRT and other modern radiation therapy techniques, the quality of the treatment can depend on the ability of the MLC to accurately form different apertures while blocking the radiation outside of the aperture. As used herein, the term radiotherapy should be broadly construed and is intended to include various techniques used to irradiate a patient, including use of photons (such as high energy x-rays and gamma rays), particles (such as electron and proton beams), and radiosurgical techniques. While modern linear accelerators use MLCs, other methods of providing conformal radiation to a target volume are known and are within the scope of the present invention.

To provide precise amounts of radiation, it is beneficial for a treatment planning system to predict accurately the dose delivered through the MLC, including any leakage. Different MLC implementations have sub-optimal geometric features causing additional leakage out of the aperture, such as interleaf leakage, residual attenuation through the leaves, irradiation through gaps between closed leaf pairs, etc. The contribution of this leakage to a delivered dose depends on the aperture shape. Leakage is of particular concern in two-layer MLCs in which the layers are offset so that the layers do not completely overlap each other.

Methods and systems are provided for determining a treatment plan for treating at least one target volume of a patient using a radiation treatment system that includes an MLC. Leaf patterns can be evaluated to compute leakage metrics including a leakage quantity indicative of a degree to which leakage would occur if the leaf patterns were used as part of a radiation treatment plan.

One embodiment of the present invention is directed to a method performed by a computer system. The method includes receiving settings for a set of leaf patterns of the MLC, each leaf pattern including a geometry of the individual leaves and forming an aperture. The method further includes identifying areas of radiation leakage in each of the leaf patterns, the areas of radiation leakage including first unshielded areas corresponding to gaps that are located between adjacent leaves and outside of the aperture. The method may further include calculating at least one leakage metric based on the areas of radiation leakage. A setting for least one of the leaf patterns can be adjusted based on the at least one leakage metric. In this way, the leaf pattern is modified to define a different pattern and the original leaf pattern is excluded from consideration. The adjustment can be performed automatically by the computer system. Adjustments can also be performed manually, e.g., by a user after reviewing one or more leakage metrics that computer system presents to the user.

Other embodiments are directed to systems and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 5B shows a second layer of an exemplary MLC plane.

DETAILED DESCRIPTION OF THE INVENTION

Figure 1:
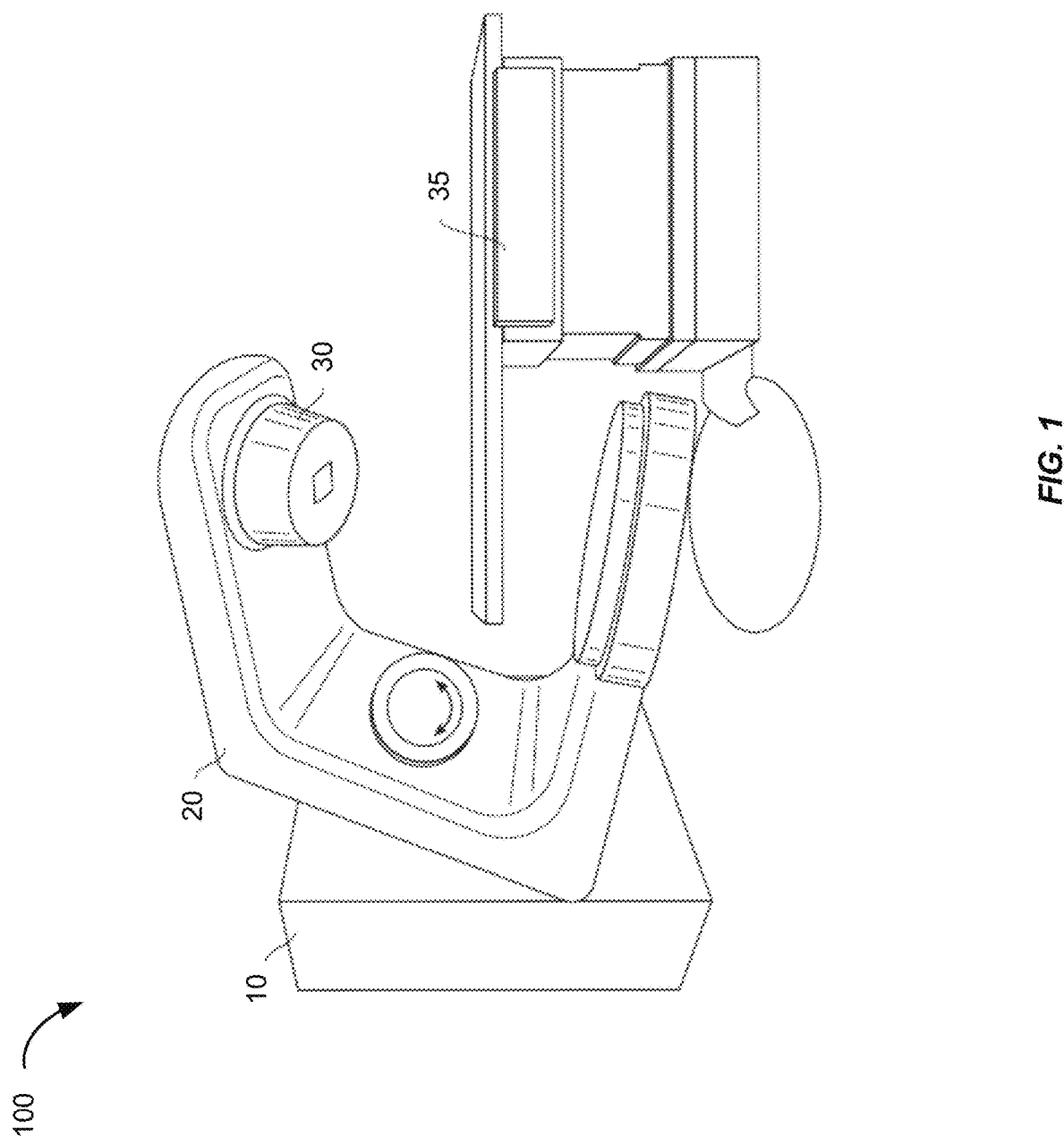
FIG. 1 is a schematic perspective view of a radiation treatment system.

The present disclosure relates generally to radiation therapy using external-beam radiation treatment systems, and is more particularly directed to evaluating leakage in MLC leaf patterns for use in forming a treatment plan. In some embodiments, leakage metrics are computed using a set of candidate leaf patterns in order to exclude leaf patterns that are associated with leakage above a threshold, e.g., by removing a leaf pattern from consideration altogether or by adjusting settings for the leaf pattern so as to define a different pattern. Leakage metrics can be computed for individual apertures, individual radiation treatment fields, or for an entire radiation treatment plan.

A radiation treatment plan or simply, "plan," generally includes a set of apertures, a set of fields, and dosage information. Each field corresponds to one or more radiation doses delivered along a given direction of incidence to a target volume (where the direction is defined by a position of a rotating gantry), each dose being delivered through a corresponding aperture. Apertures are defined by leaf patterns formed by moving the leaves of the MLC into specific configurations in accordance with settings. In static IMRT, the leaves may remain stationary while a dose is being delivered through the field, e.g., a static IMRT plan. In other plans, the leaves may be reconfigured to define a different aperture during delivery of a dose, e.g., a dynamic IMRT plan. An individual field may be associated with multiple apertures. When radiation is delivered through an aperture, a portion of the radiation gets delivered to a target volume (e.g., a tumor) within a treatment volume. The treatment volume includes a target volume intended to receive a therapeutic dose of radiation and a non-target volume intended to receive a smaller dose of radiation. Another portion of the radiation gets delivered to a non-target volume (e.g., tissue surrounding a tumor). An accurate calculation of the radiation doses delivered to the non-target volume and the target volume may be desirable. To achieve an accurate dosage calculation, the radiation contribution of areas outside of the aperture (which can be considered leakage areas) should be taken into account.

The dosage information in a radiation treatment plan can include a dose distribution, machine parameters for achieving the dose distribution for a given patient, and information about the given patient. A dose distribution provides information about the variation in the radiation dose with spatial positions within a treatment volume of the patient. A dose distribution can take many forms, e.g., a dose volume histogram (DVH) or a dose matrix. A DVH can summarize three-dimensional (3D) dose distributions in a one-dimensional (1D) format, e.g., as a 1D vector of real numbers. The DVH can be presented graphically on a two-dimensional (2D) chart, e.g., a chart where the horizontal axis is the dose (e.g., in units of grays—Gy) absorbed by a target structure (e.g., a tumor) and the vertical axis is the volume percentage. A dose matrix can provide the dose that each part of the body or the treatment volume receives. In particular, the dose matrix may describe dosage received at each voxel position in a 3D target volume that is a volume of interest, within the treatment volume, including the target structure. The dose matrix may also describe dosage received at each voxel position in a non-target volume that is located within the treatment volume, but intended to receive a smaller dose of radiation than the target volume.

I. MLC System

FIG. 1 shows a perspective view of a radiation treatment system 100. Typically, such a system is capable of generating either an electron (particle) beam or an x-ray (photon) beam for use in the radiotherapy treatment of patients on a treatment couch 35. Other radiation treatment systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) that includes control circuitry for controlling the different modes of operation of the accelerator. A high voltage source is provided within the stand or in the gantry, to supply voltage to an electron gun (not shown) positioned on an accelerator guide located in the gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Figure 2A:
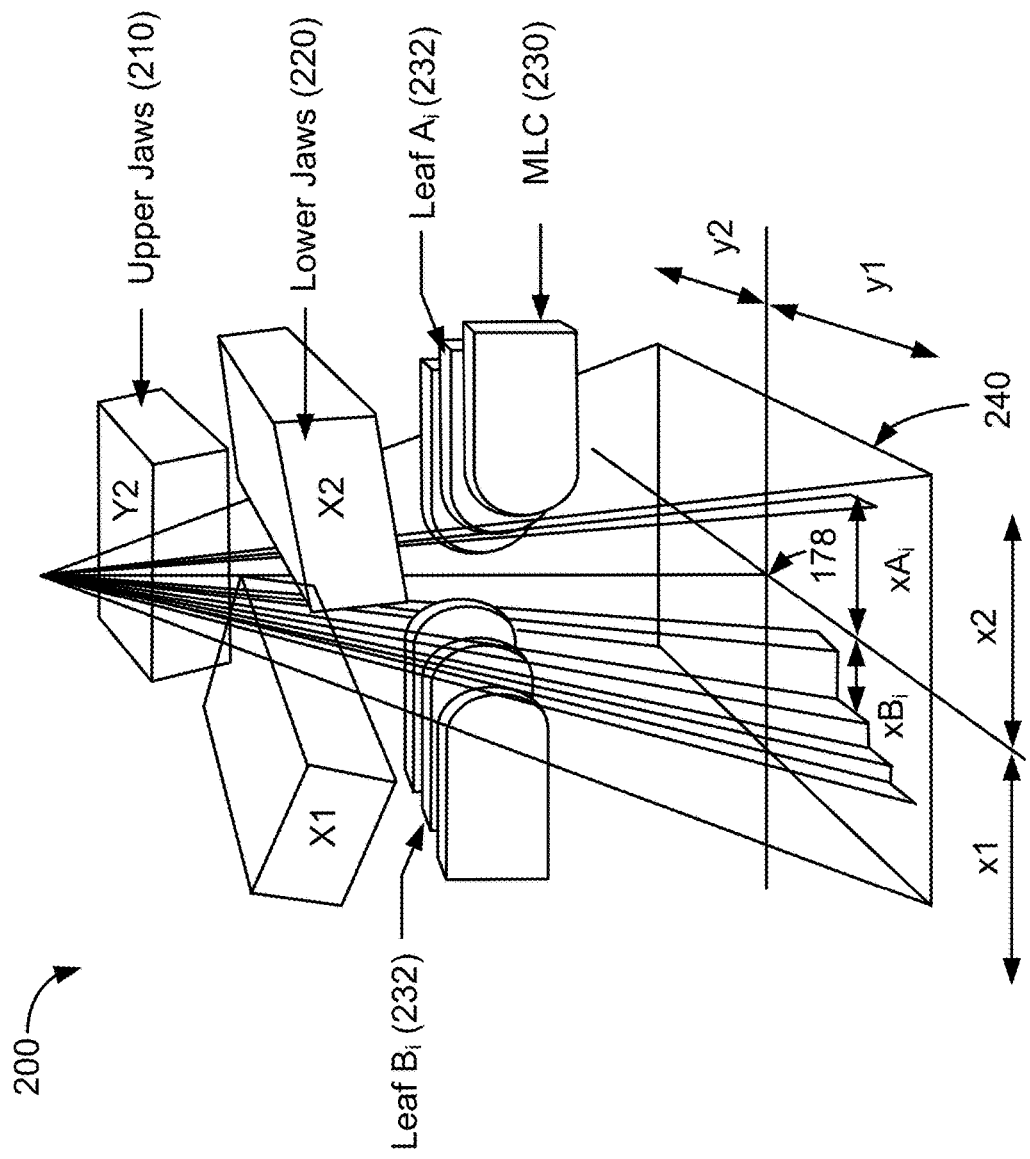
FIG. 2A shows schematically a photon collimation system in a radiation treatment system.

FIG. 2A shows schematically a photon collimation system 200 with upper jaws 210 (i.e., the Y1 and Y2 jaws; the Y1 jaw is omitted for clarity), lower jaws 220 (i.e., the X1 and X2 jaws), and an MLC 230. The field dimensions in an MLC plane 240 at an isocenter 178 are indicated. The isocenter 178 is at the intersection between the MLC plane 240 and the central axis of a beam emitted from a treatment head (not shown) of the MLC 230. The upper jaws 210, the lower jaws 220, and the leaves 232 of the MLC 230 comprise an x-ray blocking material, and are positioned in the treatment head to define the width of the x-ray beam at a patient plane (not shown). The patient plane extends across a body of the patient (e.g., a mid-coronal plane) and is usually positioned about one meter from the x-ray source or the metal target, and the axis of the gantry is located on the patient plane, such that the distance between the metal target and the isocenter 178 remains constant when the gantry is rotated. Typically, the jaws 210 and 220 are moveable and, when fully open, define a maximum beam of about 40 cm×40 cm at the patient plane. The MLC 230 is positioned at the exit of the treatment head, to further shape the x-ray beam. Current MLCs sold by the assignee of the present invention use individually controllable leaves, typically thin slices of tungsten, that can be moved into or out of the x-ray beam under the control of system software.

Figure 2B:
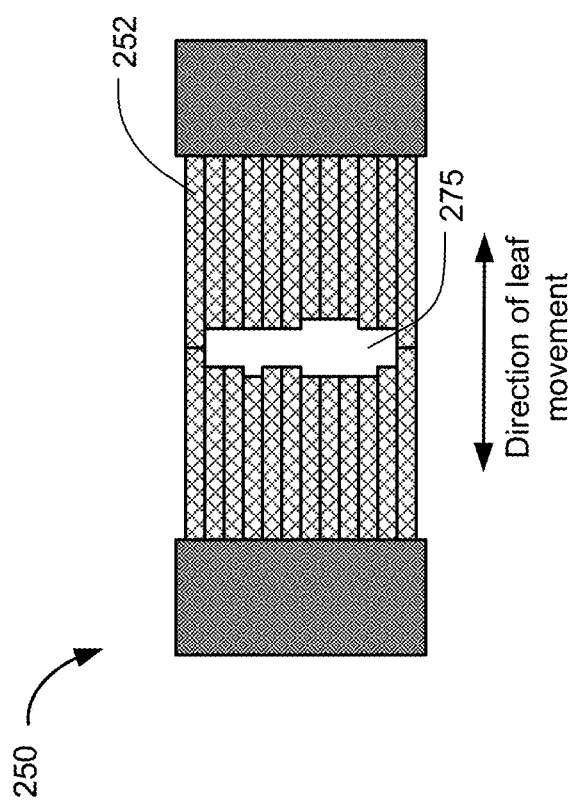
FIG. 2B shows an exemplary multileaf collimator (MLC) plane.

FIG. 2B shows an exemplary MLC plane 250 having a plurality of leaves 252, arranged in opposing pairs, and an aperture 275 created by moving the leaves 252 into a leaf pattern. Radiation passes through and is shaped by the aperture 275. Thus, the MLC can be used to collimate the x-rays to provide conformal treatment of tumors from various angles ("3D conformal") as well as intensity modulated radiotherapy ("IMRT"), whereby different radiation doses are delivered to different portions of the treatment area. The treatment volume, i.e., the irradiated volume proximate to the isocenter 178 in the path of the x-ray beam, is defined by the jaws 210 and 220, the leaf sequence of the MLC 230, and the collimator angle, i.e., the angle at which the MLC 230 sits in the treatment head. Some external radiation treatment systems may include multiple layers of MLCs. The multiple layers of MLCs may be positioned at different planes and at different collimator angles. Regardless of whether the MLC has one layer or multiple layers, there may be radiation that leaks from areas outside of the aperture into the treatment volume. As described below in connection with FIG. 6, leakage areas can include unshielded gaps through which radiation is transmitted at full strength into the treatment volume. Leakage areas can also include minimally shielded areas, e.g., areas shielded by only a single layer of leaves. In these minimally shielded areas, some of the radiation gets blocked by the leaves, but not enough to prevent the attenuated radiation from being delivered to the treatment volume in clinically significant amounts.

Figure 3:
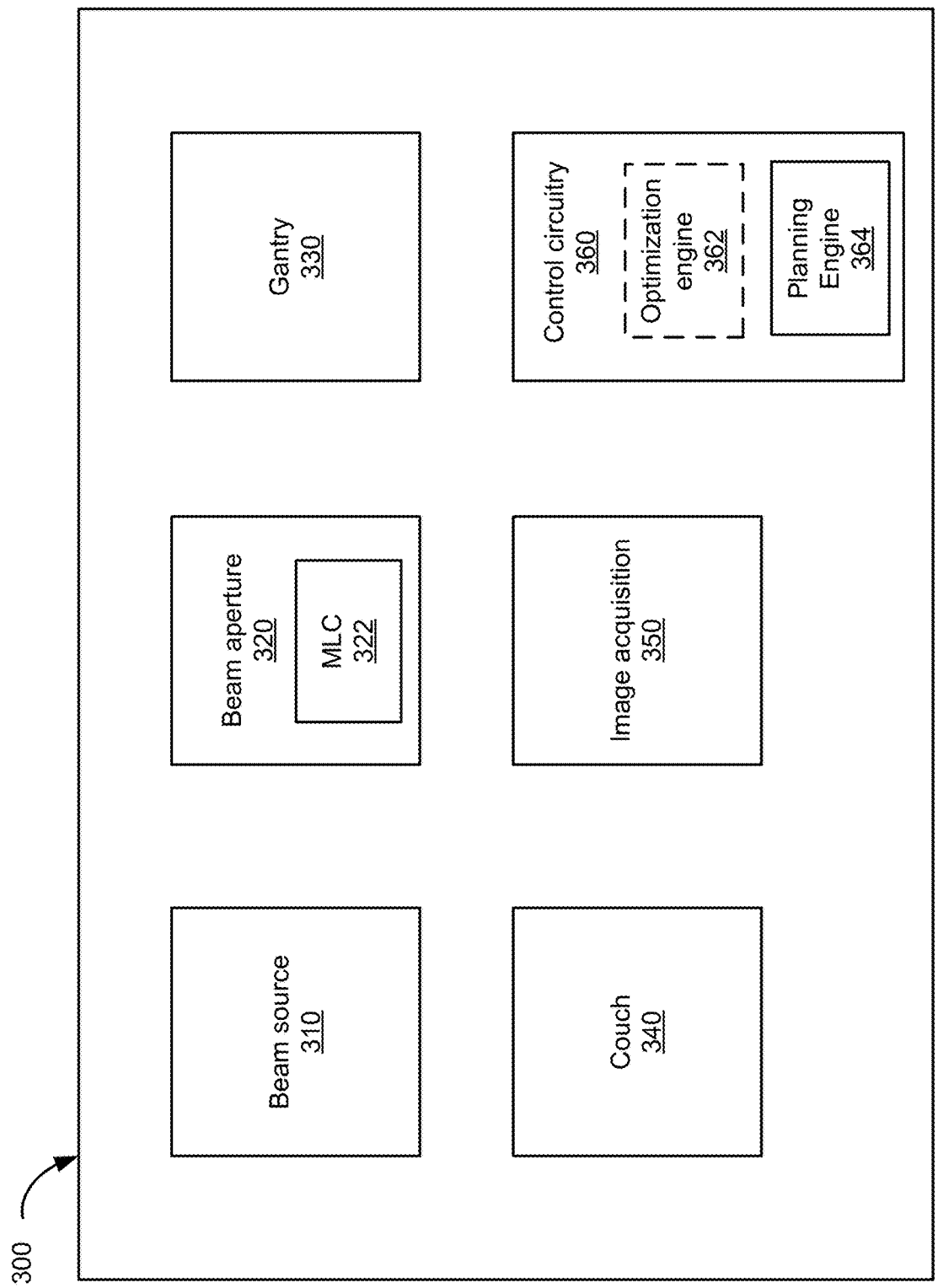
FIG. 3 shows a block diagram of a radiation treatment system according to an embodiment of the present invention.

FIG. 3 shows a block diagram of a radiation treatment system 300 according to an embodiment of the present invention. The radiation treatment system 300 includes components corresponding to those of the radiation treatment systems 100 and 200 in FIGS. 1 and 2A. For example, the radiation treatment system 300 includes a beam source 310, a beam aperture 320, a gantry 330, and a couch 340. The beam source 310 is configured to generate a beam of therapeutic radiation. This beam of radiation may include x-rays, particles, and the like. The beam aperture 320 includes an adjustable MLC 322 for spatially filtering the radiation beam. The couch 340 is configured to support and position a patient. The couch 340 may have six degrees of freedom, namely the translational offsets X, Y, and Z, and the rotation, pitch, and yaw.

The gantry 330 that circles about the couch 340 houses the beam source 310 and the beam aperture 320. The beam source 310 is optionally configured to generate imaging radiation as well as therapeutic radiation. The radiation treatment system 300 may further include an image acquisition system 350 that comprises one or more imaging detectors mounted to the gantry 330.

The radiation treatment system 300 further includes a control circuitry 360 for controlling the operation of the beam source 310, the beam aperture 320, the gantry 330, the couch 340, and the image acquisition system 350. The control circuitry 360 may include hardware, software, and memory for controlling the operation of these various components of the radiation treatment system 300. The control circuitry 360 can comprise a fixed-purpose hard-wired platform or can comprise a partially or wholly-programmable platform. The control circuitry 360 is configured to carry out one or more steps, actions, and other functions described herein. In some embodiments, the control circuitry 360 may include a memory for receiving and storing a radiation treatment plan that defines the control points of one or more treatment fields. The control circuitry 360 may then send control signals to the various components of the radiation treatment system 300, such as the beam source 310, the beam aperture 320, the gantry 330, and the couch 340, to execute the radiation treatment plan.

In some embodiments, the control circuitry 360 may include an optimization engine 362 configured for determining a radiation treatment plan. In other embodiments, the control circuitry 360 may not include an optimization engine. In those cases, a radiation treatment plan may be determined by an optimization engine in a separate computer system, and the radiation treatment plan is then transmitted to the control circuitry 360 of the radiation treatment system 300 for execution. When an optimization engine is included, the optimization engine may communicate with a planning engine 364 to, for example, compute a dose volume histogram or dose matrix taking into consideration a leakage dose or a leakage metric.

The control circuitry 360 may further include a planning engine 364 configured for determining leakage associated with a treatment plan. As described below in connection with the method of FIG. 11, output of the planning engine 364 may be supplied to the optimization engine 362 for revising a treatment plan based on the leakage metrics described herein.

Figure 4:
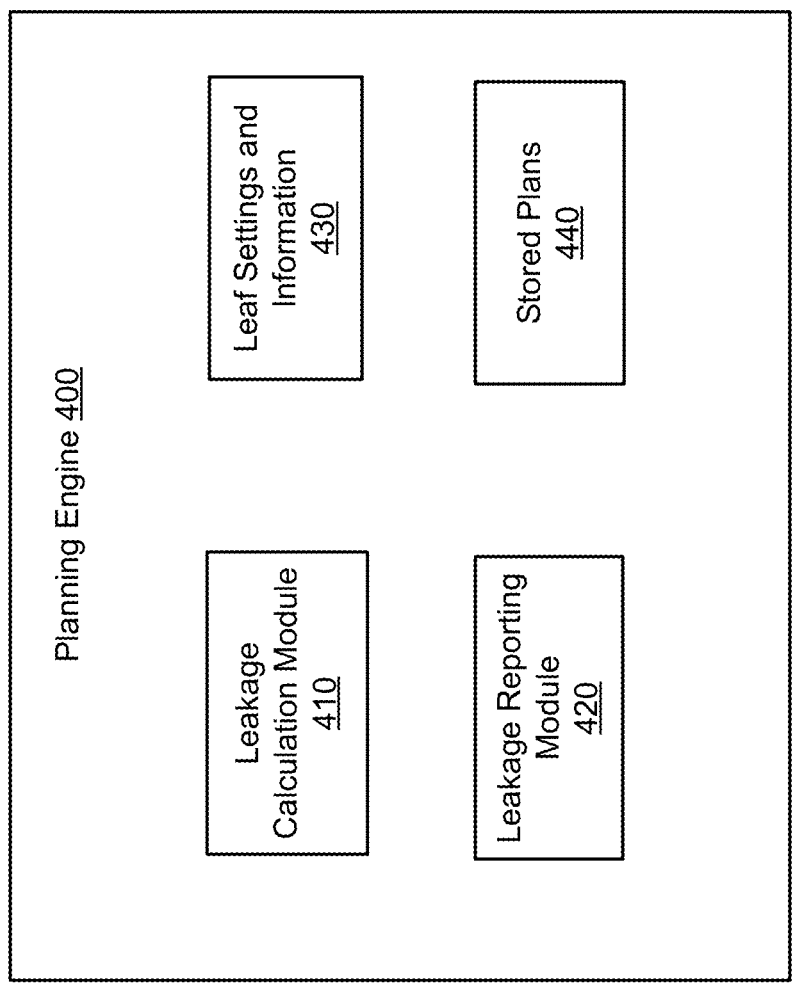
FIG. 4 shows a block diagram of a planning engine according to an embodiment of the present invention.

FIG. 4 shows a block diagram of a planning engine 400 according to an embodiment of the present invention. The planning engine 400 includes a leakage calculation module 410, a leakage reporting module 420, leaf settings and information 430, and stored plans 440. In some embodiments, the leaf settings and information 430 and the stored plans 440 may be stored together in a separate memory in the radiation treatment system or external to the radiation treatment system. The leakage calculation module 410 is configured to calculate leakage metrics for the stored plans 440, using the leaf settings and information 430. As described below, leakage metrics may include scalar leakage values computed for individual apertures, for all the apertures of a given field, or for all the apertures of a given treatment plan. In some embodiments, the metrics are values associated with a 2D matrix characterizing leakage at different positions along a plane, e.g., the MLC plane 240 in FIG. 2A. In other embodiments, the metrics are values associated with a 3D leakage dose matrix characterizing a leakage dose delivered into a 3D volume of interest, e.g., a target volume. The 3D leakage dose matrix is analogous to the dose matrix described earlier at the beginning of this detailed description, but corresponds to an additional dose of unwanted radiation delivered, as a result of leakage, into the volume of interest.

The leaf settings and information 430 describe various leaf patterns that define apertures selectable for inclusion as part of a radiation treatment plan. For example, the leaf settings and information 430 may include settings for aspects of the leaf patterns that are adjustable, such as the position of each leaf in a given leaf pattern. The leaf settings and information 430 may further include information about aspects of the leaf patterns that are fixed, such as leaf length, width, and thickness.

The leakage reporting module 420 is configured to output results of the leakage calculation module 410 for storage or processing by another component of the radiation treatment system, such as the optimization engine 362. In some embodiments, the results are output to a computer display for visualization of leakage metrics. Any of the leakage metrics described herein can be output for display, including display in a numerical format (e.g., a list or table of leakage values), a graphical format (e.g., a 2D or 3D chart), or a combination of numerical and graphical formats. For example, a 2D or 3D leakage matrix may be displayed with numeral values representing leakage at each position in the matrix. The numerical values may be supplemented or replaced by color coding the numerical values, e.g., using different colors to represent the degree of leakage. The matrix may be overlaid over an acquired image or a graphical representation of the treatment volume or the target volume. In some embodiments, the leakage reporting module 420 may provide a summary of a leakage analysis. The summary may include, for example, leakage metrics for individual apertures, fields, or plans. The summary may also include an indication of which apertures, fields, or plans meet leakage constraints. If a leakage matrix is computed, the summary may include which matrix positions meet or fail to meet leakage constraints.

II. Leakage Areas in a Two-Layer MLC

A single layer of leaves was discussed above. In some embodiments, the MLC may include multiple layers (e.g., a proximal layer and a distal layer) that combine to form an aperture. Leakage calculation, in accordance with an embodiment of the present invention, may be performed for single or multi-layer MLCs. An example of a multi-layer MLC is now described in connection with FIGS. 5A and 5B. In a multi-layer MLC, the layers may be laterally offset so that the ability of a proximal layer to provide additional shielding for a distal layer depends on small scale (single leaf resolution) geometries.

Figure 5A:
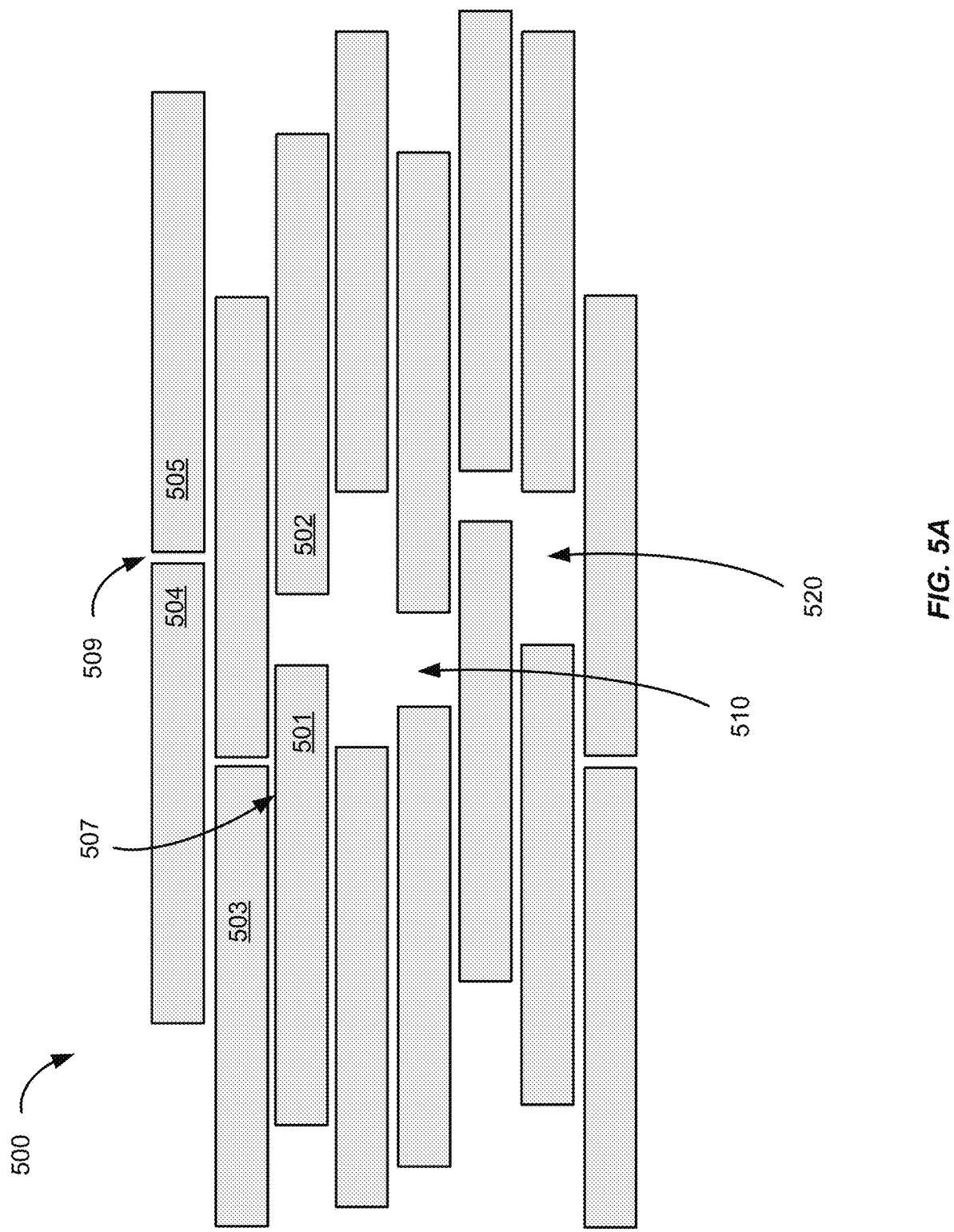
FIG. 5A shows a first layer of an exemplary MLC plane.

In FIGS. 5A and 5B the leaves are not drawn to scale and the leaves may be longer than depicted. In the MLC 230 of FIG. 2A, the treatment volume, i.e., the irradiated volume proximate to the isocenter in the path of the x-ray beam, is defined by the jaws 210 and 220, the leaf pattern of the leaves 232, and the collimator angle (i.e., the angle at which the MLC 230 sits in the treatment head). Similarly, a treatment volume of a multi-layer MLC may be defined by a set of jaws, the leaf patterns of multiple layers of leaves, and a collimator angle. The multiple layers may be positioned at different MLC planes and at different collimator angles. Example leakage metrics described herein relate to leakage observed at an MLC plane. In some embodiments, the leakage metrics relate to a "leakage dose," i.e., an unwanted dose of radiation, delivered into a treatment volume.

FIG. 5A shows a first layer 500 of an exemplary MLC plane. The layer 500 corresponds to a distal layer. As shown in FIG. 5A, the leaves are arranged in a specific pattern to define one or more openings 510 and 520 that, when combined with openings in a proximal layer (shown in FIG. 5B), form an aperture through which radiation is delivered. The leaf pattern is formed by positioning opposing pairs of leaves to form the openings 510 and 520. For example, opposing leaves 501 and 502 form part of the opening 510. In areas where no opening is desired, the opposing leaves can be moved as closely together as permitted by the MLC.

Because of leaf geometries (e.g., the edges of the leaves may not be perfectly straight) and limitations on the ability of the MLC to precisely position the leaves, there may be unwanted gaps between adjacent, opposing leaf pairs. For example, there is a gap 509 between leaf 504 and its opposing leaf 505, even though the leaves 504 and 505 are supposed to be fully closed. Similarly, there are unwanted gaps between adjacent leaves that are not of the same pair, corresponding to spaces between the longitudinal edges of the leaves. For example, in FIG. 5A, there is a gap 507 between a leaf 501 and its adjacent leaf 503. The unwanted gaps are small relative to the size of the leaves. For example, when projected into the plane of the isocenter, a typical leaf width ranges from 5 millimeters to 1 centimeter, while the gap between longitudinal edges may be around 20 microns, and the gap between a fully closed leaf pair is around half a millimeter. Nevertheless, these unwanted gaps are a source of leakage.

FIG. 5B shows a proximal layer 530 of the exemplary MLC plane in FIG. 5A. As with the leaves in the distal layer 500, the leaves can be individually positioned to form a leaf pattern defining one or more openings based on the distance between opposing leaves, e.g., leaves 521 and 523. In FIG. 5B, the leaves form a single opening 550. Similar to FIG. 5A, there are unwanted gaps between adjacent, opposing leaves (e.g., gap 519) and unwanted gaps between adjacent leaves not of the same pair (e.g., gap 517). Although the leaves of the distal layer 500 are shown as being the same size and shape as the leaves of the proximal layer 530, the leaf geometries need not be the same. For example, in some embodiments, the leaves in the distal layer may have a different geometry than the leaves in the proximal layer. Leaf geometry may also vary within a given layer. For simplicity, the leakage metrics described herein have been described with respect to leaves sharing the same geometry.

Figure 5C:
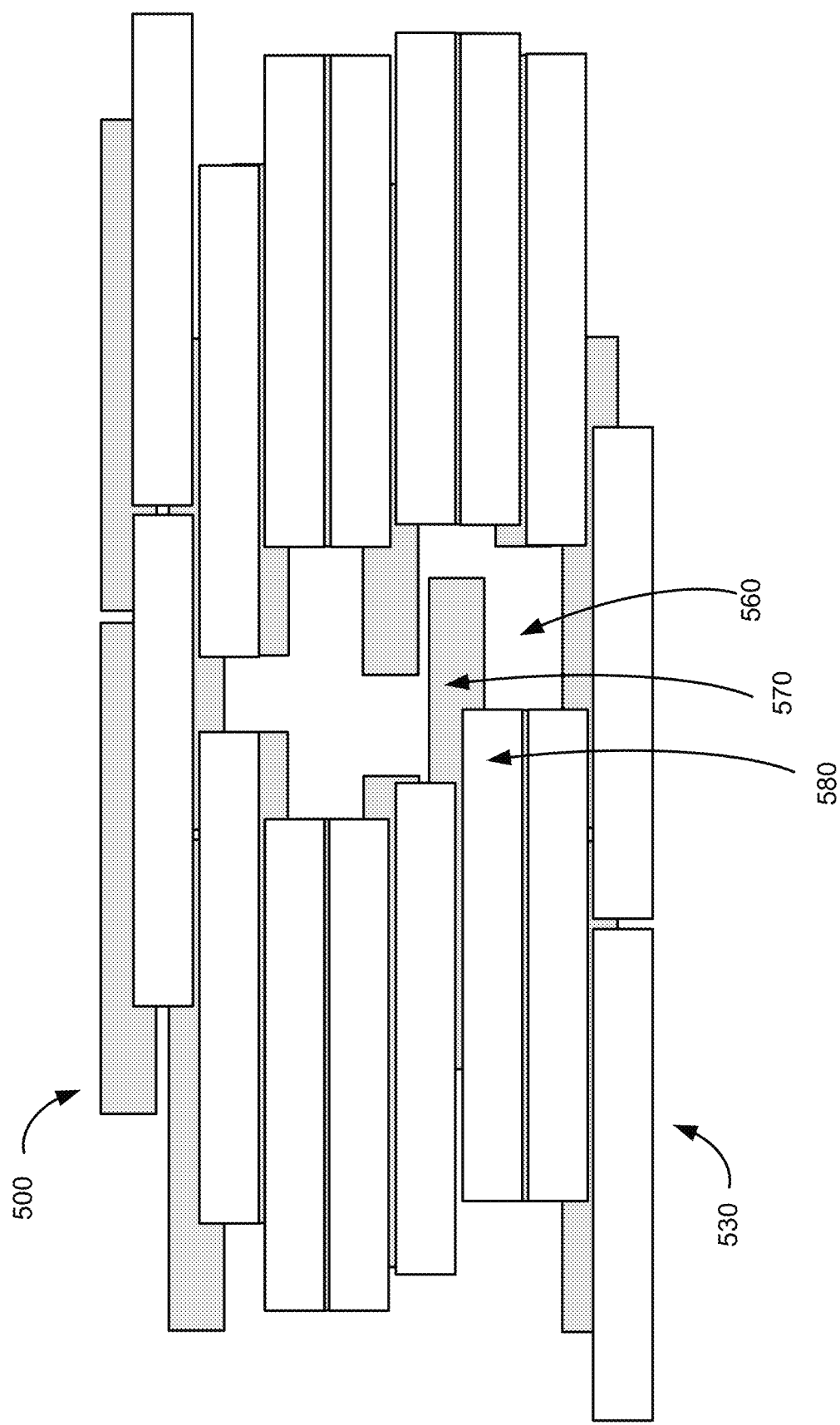
FIG. 5C shows an aperture formed by the layers of FIGS. 5A and 5B.

FIG. 5C shows an aperture formed by combining the distal layer 500 in FIG. 5A and the proximal layer 530 in FIG. 5B. The distal layer 500 and the proximal layer 530 are laterally offset, e.g., by a distance equal to half a leaf width. As a result, the leaves of the proximal layer 530 do not completely overlap the leaves of the distal layer 500. As shown in FIG. 5C, the combination of the distal layer 500 and the proximal layer 530 produces areas that are not shielded by any layer, e.g., area 560. These unshielded areas include the aperture plus unwanted leakage areas. The combination of layers 500 and 530 also includes areas that are shielded by a single layer (e.g., area 570, corresponding to a leaf in the distal layer 500) and areas that are shielded by two layers (e.g., area 580). In a typical MLC, shielding by two layers is usually sufficient to ensure a negligible amount of leakage. For example, double-layer shielded areas may leak around 0.01% of the radiation delivered. Shielding by a single layer results in a small, but clinically significant, amount of leakage (e.g., 1%), which can be taken into consideration when calculating a leakage metric in accordance with an embodiment of the present invention.

Figure 6:
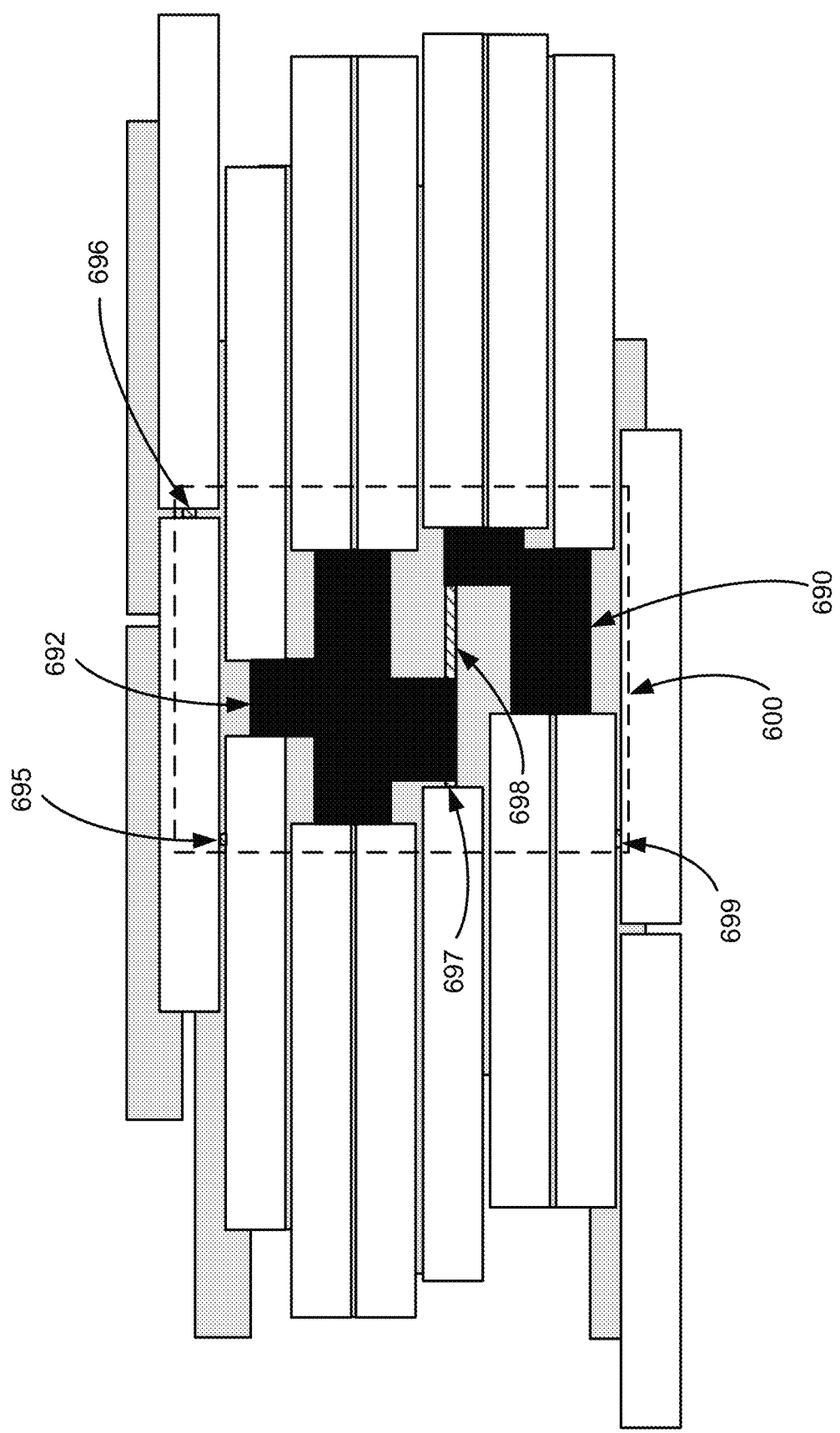
FIG. 6 shows leakage areas around the aperture of FIG. 5C.

FIG. 6 shows various leakage areas around the aperture of FIG. 5C. In FIG. 6, the aperture is shown as solid black areas 690 and 692. For leakage calculation purposes, unshielded areas and single-layer shielded areas that are situated around the aperture can be taken into consideration by treating these areas as leakage areas. The area around the aperture is shown in FIG. 6 as an area 600, using broken lines, and includes unshielded areas corresponding to gaps between adjacent leaves, e.g., areas 695 to 699. Unshielded areas and single-layer shielded areas located outside of the area 600 are not taken into consideration because little or no radiation is delivered outside of area 600.

Various methods are now described in connection with a two-layer MLC, but can be readily adapted for use with a single layer MLC or multi-layer MLCs having more than two layers. Although the two-layer MLC structure in FIG. 5C was described as having negligible leakage in double-layer shielded areas, certain multi-layer MLC implementations may not provide adequate shielding even when an area is shielded by two layers, for example, when the leaves are very thin or made of a material with lower x-ray blocking ability than tungsten. Thus, the methods are not to be construed as being limited to use with a two-layer MLC. The methods may be performed by the radiation treatment system 300 of FIG. 3 and the planning engine 400 of FIG. 4.

III. Method of Determining Treatment Plan Based on Leakage

Figure 7:
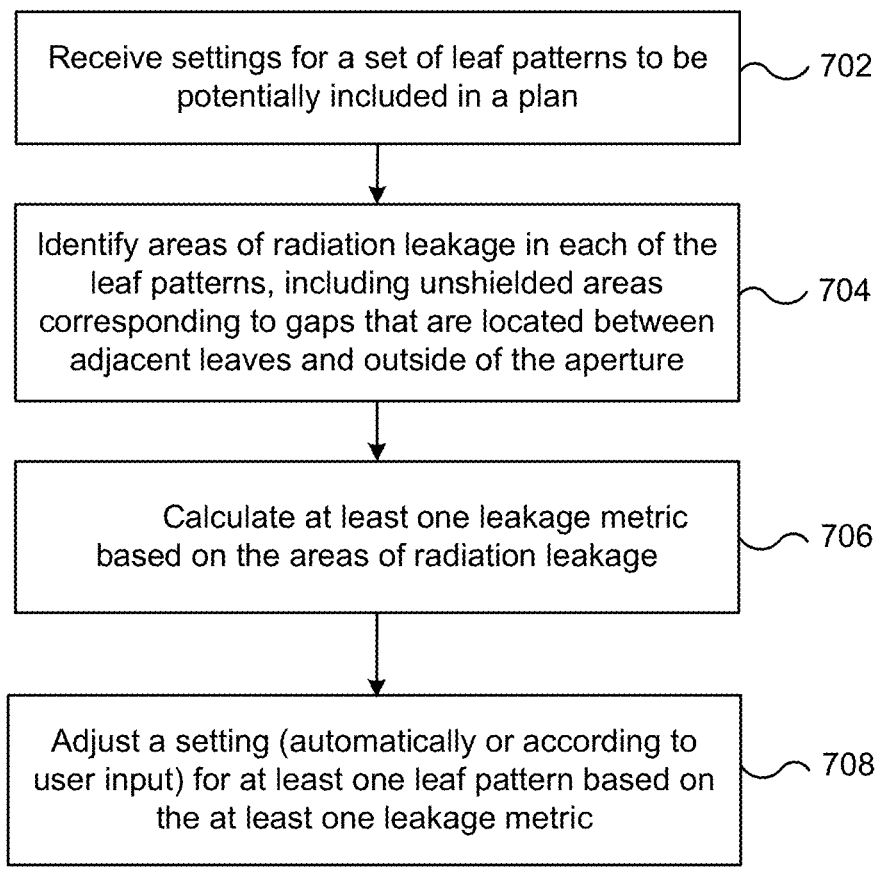
FIG. 7 is a flowchart illustrating a method for determining a treatment plan for treating at least one target volume of a patient using a radiation treatment system that includes an MLC, according to an embodiment of the present invention.

FIG. 7 is a flowchart illustrating a method 700 for determining a treatment plan for treating at least one target volume of a patient using a radiation treatment system that includes an MLC, according to an embodiment of the present invention.

In step 702, settings are received, from a user or the optimization engine 362, for a set of leaf patterns to be potentially included in a radiation treatment plan. If the settings are received from a user, the settings can be supplied through a user interface of a computer. If the settings are received from the optimization engine 362, they can be transmitted through internal communication between the optimization engine 362 and the planning engine 400. For example, the planning engine 400 can receive, from the user or the optimization engine 362, a list of candidate leaf patterns for which leakage is to be evaluated, along with corresponding settings for the candidate leaf patterns, and can store the settings as part of the leaf settings 430. As described earlier, the leaf settings 430 may include information about the position of each leaf in a given leaf pattern, in addition to information about leaf geometry.

In step 704, areas of radiation leakage are identified for each of the leaf patterns for which settings were received in step 702. The leakage areas correspond to areas, in an MLC plane, for which there are clinically significant amounts of leakage. For example, as described above in connection with FIG. 6, the leakage areas may correspond to unshielded and single-layer shielded areas around the outside of the aperture. Thus, the leakage areas may be identified (e.g., by analyzing a computer representation of the 2D layout of a leaf pattern) to determine which pixels or coordinates in the layout are assigned to one layer, which are assigned to two or more layers, and which have no layers assigned.

In step 706, at least one leakage metric is calculated based on the leakage areas identified in step 704. The computation of leakage metrics is described in the next section, in connection with FIGS. 8 to 10. As will be explained, example leakage metrics include leakage values that represent leakage associated with an aperture, a field, or a plan. The leakage metrics may also include leakage values characterizing (e.g., in the form of a 2D matrix) leakage as a function of spatial position along a plane. The leakage metrics may further include leakage values characterizing (e.g., in the form of a 3D matrix) leakage as a function of spatial position in a 3D volume of interest, e.g., a target volume. In some embodiments, the leakage metrics include scalar quantities that summarize the values contained in a 2D or 3D matrix.

In step 708, a setting for at least one leaf pattern is adjusted based on the leakage metric(s) calculated in step 706. The leaf pattern setting may be adjusted, for example, in response to exceeding a threshold predefined for a given leakage metric. In the case of a 2D or 3D matrix, the settings for one or more leaf patterns associated with the matrix may be adjusted when the threshold is exceeded for any given position in the matrix. Alternatively, the leaf pattern settings may be adjusted in response to a certain number or percentage of positions exceeding the threshold. In this manner, leaf patterns may be ruled out as candidates, thereby narrowing the list of patterns that can be potentially included in the treatment plan, while also defining new patterns. The adjustment can be performed automatically, e.g., by programming the radiation treatment system with instructions to define a smaller aperture by selecting one or more leaves and moving the one or more leaves closer toward the center of the aperture. In some embodiments, the planning engine 400 may perform the adjustment by referencing a threshold stored in a memory of the radiation treatment system. Stored thresholds can be configurable, e.g., in real-time while radiation is being delivered during treatment or when the radiation treatment system is offline.

Additionally, as described below in connection with FIG. 11, leakage metrics or leakage matrices can be input to the optimization engine 362 in order to revise a treatment plan, e.g., by adjusting settings of leaf patterns. The optimization engine 362 may take the leakage metrics into consideration when optimizing the treatment plan, for example by incorporating the leakage metrics into a dose distribution calculation, so that leaf patterns which cause the treatment plan to fail to meet dosage constraints are refined. Thus, the adjustment of leaf pattern settings can be performed by both the optimization engine 362 and the planning engine 400.

Manual adjustments are also possible. For example, the radiation treatment system 300 can present one or more leakage metrics to the user via a display, e.g., graphically or as text. After reviewing the one or more leakage metrics, the user may decide to adjust the settings of one or more leaf patterns. The display can include a user interface configured to receive user input for making an adjustment, e.g., by dragging a graphical representation of a leaf to a new position or entering a numerical value that specifies the position of the leaf. Accordingly, the adjustment based on the at least one leakage metric may occur as a result of displaying a graphical representation of a leakage metric and receiving an adjustment of the settings from a user via a user interface.

The remaining apertures can then be input to the optimization engine 362 to determine treatment parameters for use with the remaining apertures. For example, the optimization engine 362 may calculate an optimal beam duration and an optimal beam intensity for each aperture in a given field, a treatment head angle for each field, and a sequence in which the leaves are moved (e.g., a sequence defining the order in which the apertures are formed). In some embodiments, treatment parameters can be determined prior to adjusting leaf pattern settings, in which case the optimization engine 362 can modify the predetermined treatment parameters to take into account the subsequent modification of one or more leaf patterns. After optimization is completed, the resulting treatment plan can include a set of remaining apertures and one or more fields (each field being assigned a subset of the remaining apertures), gantry and couch positions for each field, and dosage information indicating, e.g., a beam duration and/or a beam intensity for each aperture. The leakage metrics may also be used as an indication of the expected amount of excess radiation that would occur if the treatment plan were used, thus predicting leakage. When the treatment plan is ready to be executed by the radiation treatment system 300, the plan can be transmitted from storage (e.g., from the stored plans 440) to the control circuitry 360 for controlling the operation of the beam source 310, the beam aperture 320, the gantry 330, the couch 340, and the image acquisition system 350, in accordance with the plan.

IV. Computation of Leakage Metrics

Example leakage metrics for characterizing the amount of radiation delivered through leakage areas will now be described. The leakage metrics include scalar leakage metrics that characterize leakage using single numerical values associated with a given aperture, field, or plan. As will be explained, the leakage metrics can be derived from the geometries of the leaf patterns or using geometry in combination with information about how much radiation is delivered through a given leakage area.

A. Scalar Leakage Metric based on Leakage Areas

Figure 8:
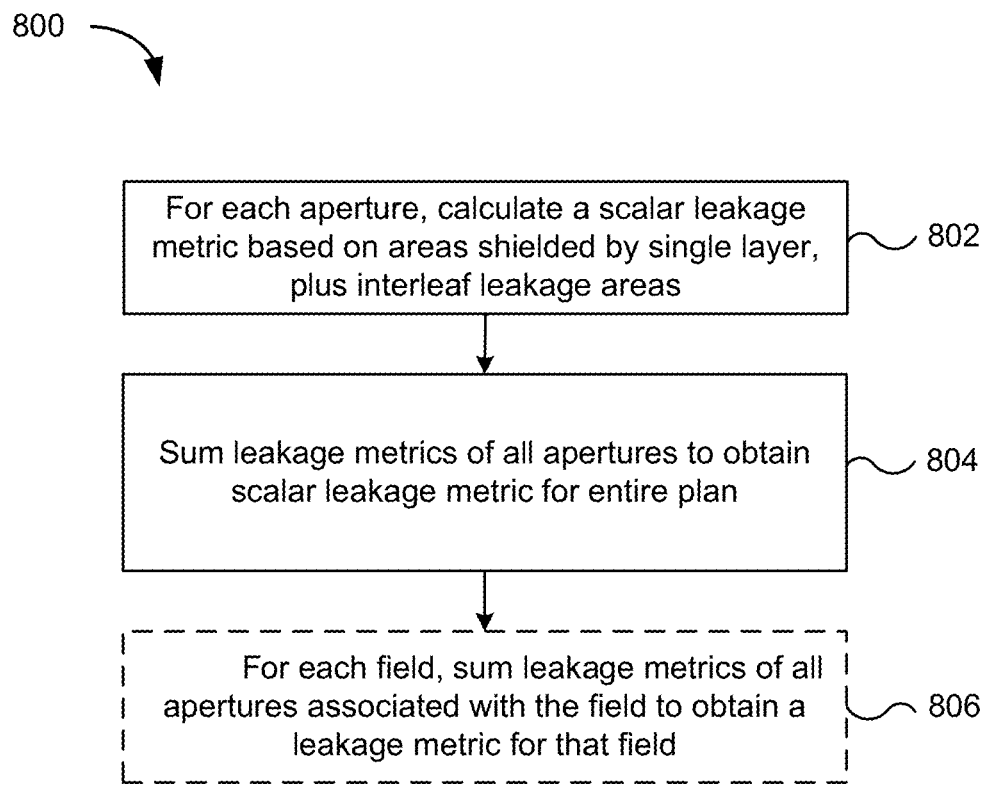
FIG. 8 is a flowchart illustrating a method for computing a scalar leakage metric, according to an embodiment of the present invention.

FIG. 8 is a flowchart illustrating a method 800 for computing a scalar leakage metric, according to an embodiment of the present invention. The method 800 can be performed to implement the leakage calculation in step 706 of the method 700, or as part of step 1102 in the method of FIG. 11.

In step 802, a scalar leakage metric may be calculated for each aperture, based on leakage areas including single-layer shielded areas and areas of interleaf leakage between adjacent leaves. For example, equation (1) defines a metric $C_{2d}$ describing leakage through single-layer shielded areas, plus interleaf leakage:

$$C_{2d} = A_{SL}R_{SL} + L_{IL}r_{IL} \quad (1)$$

where $A_{SL}$ is the total area covered by only a single layer, $R_{SL}$ is the leakage radiation through a single layer for a unit area, $L_{IL}$ is the total length of the interleaf leakage areas (the summed lengths of the gaps between two adjacent leaves not covered by the leaves in another layer, e.g., the gaps 695 to 699 in FIG. 6), and $r_{IL}$ is an interleaf leakage radiation quantity for a unit distance. The radiation leakage coefficients $R_{SL}$ and $r_{IL}$ may be predetermined, for example, based on measurements using the MLC.

In equation (1), the second term is based on length because the gaps that form the interleaf leakage areas are very thin and can therefore be approximated as lengths. However, it is also possible to substitute an area term, e.g., by summing the interleaf leakage areas. In some embodiments, leakage metrics are normalized by, for example, dividing a leakage value by the total area of a desired aperture (e.g., the sum of the areas 690 and 692 in FIG. 6). A normalized leakage metric provides a sense of leakage relative to delivered radiation, which can be useful for assessing how much leakage is occurring in relation to a delivered dose, whereas a non-normalized leakage metric may be useful for a purely quantitative assessment of leakage.

In step 804, the leakage metrics $C_{2d}$ calculated in step 802 may be summed for all apertures to obtain a leakage metric $C_{2d}^{plan}$ for an entire plan comprising multiple apertures:

$$C_{2d}^{plan} = \Sigma_i C_{2d}^i \quad (2)$$

where i is the i-th aperture. Each aperture i has its own $A_{SL}$ and $L_{IL}$.

In step 806, a scalar metric may optionally be calculated for each field by summing the leakage metrics $C_{2d}^{plan}$ for all apertures associated with a given field:

$$C_{2d}^{field} = \Sigma_i C_{2d}^i \quad (3)$$

The metric in equation (3) is particularly useful for IMRT applications, where radiation is typically delivered from many directions into the treatment volume through different sets of apertures. A similar metric can be derived for arc therapy by using raying tracing to define the leakage areas based on the intersection of leakage paths that pass through unshielded and single-layer shielded areas as the gantry is moved.

The metrics $C_{2d}$, $C_{2d}^{plan}$, and $C_{2d}^{field}$ can be used to adjust leaf pattern settings in step 708 of the method 700. For example, a leaf pattern can be modified or removed from consideration if its corresponding metric $C_{2d}$ is above a certain threshold, indicating that radiation would not be sufficiently contained within the area of the aperture. Similarly, if the metric $C_{2d}^{field}$ is above a certain threshold, the entire set of leaf patterns associated with the field may be excluded from being used in combination with each other, i.e., the entire field can be invalidated. The leakage threshold for fields is generally higher than that of an individual aperture. Thus, even though the individual apertures of a given field may meet the aperture threshold requirement, the field as a whole may fail because the cumulative leakage represented by $C_{2d}^{field}$ is too large, indicating that excessive radiation would be delivered outside of the apertures over a course of treatment.

Similarly, the threshold for $C_{2d}^{plan}$ is generally higher than the threshold for $C_{2d}^{field}$ and can be used as a basis for excluding the entire set of leaf patterns associated with the plan. If an entire plan is invalidated in this manner, the planning engine 400 can select an alternative plan for leakage analysis or, if no alternative plans are available, the planning engine 400 can request a plan revision from the user or the optimization engine 362. In some embodiments, individual leaf patterns are modified or removed from consideration when $C_{2d}^{plan}$ or $C_{2d}^{field}$ exceed their corresponding thresholds, instead of excluding leaf pattern sets. For example, if the threshold for $C_{2d}$ is met with respect to all the apertures in a field, but the threshold for $C_{2d}^{field}$ is not met, then the user or the optimization engine 362 can attempt to bring the field into compliance with the field threshold by, e.g., selecting one or more leaf patterns for removal from the plan or exclusion from being used with that particular field, or by modifying a leaf pattern to reduce the leakage areas.

B. 2D Leakage Fluence Matrix

Figure 9:
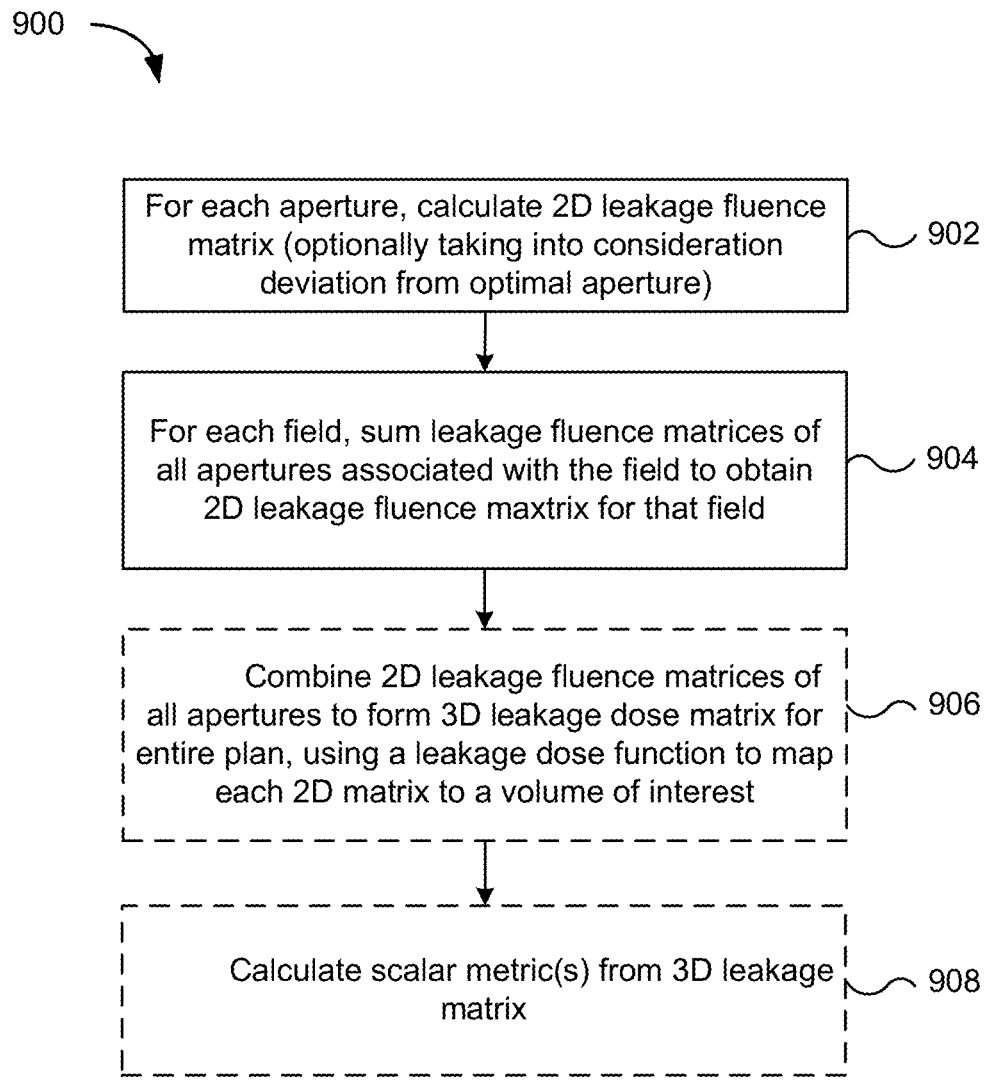
FIG. 9 is a flowchart illustrating a method for computing a leakage matrix, according to an embodiment of the present invention.

FIG. 9 is a flowchart illustrating a method 900 for computing a leakage matrix, according to an embodiment of the present invention. The method 900 may be performed in addition, or as an alternative, to the method 800.

In step 902, a 2D "leakage fluence" matrix $F_{2d}^i$ may be calculated. Each entry in the matrix $F_{2d}^i$ corresponds to a pixel in the plane of an aperture, and the value of the pixel corresponds to the fluence at that pixel. The size of each pixel can be arbitrarily defined as a small region surrounding the pixel coordinate. In some embodiments, the pixel size is the same as pixels in the 2D layout from which the leakage areas were determined in step 704 of the method 700. The pixel resolution can be variable, e.g., in some embodiments the user can elect to have a different pixel size, and can adjust the size of the pixels accordingly. Fluence refers to the number of radiated particles per unit area and is usually calculated by integrating flux (a measure of the rate of particle flow through a unit area) over time. In radiation therapy planning, an energy fluence is sometimes used in dose calculations to determine the delivered dose. Analogously, leakage fluence is used herein to represent the number of radiated particles leaking through a unit area. Thus, the matrix $F_{2d}^i$ characterizes the amount of leakage radiation received by a surface on a per unit area basis. In this instance, the surface corresponds to the plane of the aperture i.

The matrix $F_{2d}^i$ can be calculated by excluding the radiation contributions of areas corresponding to the desired aperture (e.g., the areas 690 and 692 in FIG. 6). Each entry (j,k) of the matrix $F_{2d}^i$ can be calculated as follows:

$$F_{2d}^i(j,k) = A_{SL}(i,j,k)R_{SL} + L_{IL}(i,j,k)r_{IL} \quad (4)$$

Each matrix entry (j,k) corresponds to a fluence pixel whose value represents a sum or average of leakage through a small region around $(x_j, y_j)$, where $(x_j, y_j)$ corresponds to the spatial coordinates of a location on the aperture plane. Similar to equation (1) above, $A_{SL}(i,j,k)$ and $L_{IL}(i,j,k)$ are the total area of single-layer coverage and the length of interleaf leakage, respectively, in the region around the coordinate $(x_j, y_j)$ for aperture i. The matrix $F_{2d}^i$ may optionally be calculated taking into consideration a deviation from an optimal aperture. The deviation introduces an additional term into equation (4) and is described in detail below in section D.

In step 904, a 2D leakage fluence matrix $F_{2d}^{field}$ may be calculated for a given field by summing the matrix entries in equation (4) over all apertures i associated with the field:

$$F_{2d}^{field}(j,k) = \Sigma_i F_{2d(j,k)}^i \quad (5)$$

Once calculated, the matrices $F_{2d}^i$ and $F_{2d}^{field}$ can be stored (e.g., in a memory assigned to the leakage calculation module 410) for subsequent use by the planning module 400 or the optimization engine 362. In some embodiments, the matrices $F_{2d}^i$ and $F_{2d}^{field}$ can be stored in association with a corresponding plan in the stored plans 440.

C. 3D Leakage Dose Matrix

Continuing the method 900 in FIG. 9, in step 906, the 2D matrices $F_{2d}^i$ of all the apertures may optionally be combined to form a 3D leakage dose matrix $C_{3d}$ for an entire plan, using a "leakage dose" function to map each matrix into a 3D volume of interest, e.g., the treatment volume or the target volume. The leakage dose function is applied to each 2D matrix $F_{2d}^i$ individually to form a 3D matrix for each 2D matrix. The individual 3D matrices can then be combined by summing values at corresponding voxel locations to form a 3D leakage dose matrix $C_{3d}$. The 3D leakage dose matrix $C_{3d}$ can be calculated as follows:

$$C_{3d} = \Sigma_i D(F_{2d}^i) \tag{6}$$

where D is a leakage dose function analogous to a dose function used for calculating a 3D dose matrix from energy fluence. Dose functions are usually implemented as a series of calculations according to an algorithm that takes into account various factors such as variations in particle scattering due to heterogeneity in patient tissues. For example, the algorithm may compute a delivered dose based on a convolution model in which a fluence value of a photon or particle is convolved with an energy deposition function and a scatter kernel to form an absorbed energy value for a given point in the volume of interest. The fluence value, energy deposition function, and scatter kernel are defined for a finite-sized beamlet that forms part of the radiation beam emitted by the source. The energy deposition function corresponds to an area integral of the energy deposited over a surface at a certain depth in the volume of interest. The scatter kernel represents lateral energy scattering and may factor in tissue heterogeneity. The absorbed energy value, which is expressed in units of Joules per cubic meter ($J/m^3$), is then converted into a dose value in units of grays (Gy).

Each 2D leakage fluence matrix $F_{2d}^i$ is mapped to the volume of interest by the leakage dose function D, producing a corresponding 3D leakage dose matrix. As with the matrices $F_{2d}^i$ and $F_{2d}^{field}$, the 3D leakage dose matrix $C_{3d}$ can be stored for subsequent use by the planning module 400 or the optimization engine 362. In some embodiments, the leakage dose function D can be a simplified function, e.g., it does not need to factor in all of the variables or parameters (e.g., heterogeneity) that would normally be used in computing a delivered dose, so long as the leakage dose function D operates to map the leakage fluence to the volume of interest. The resulting 3D matrices are then summed, according to equation (6), to form the 3D leakage dose matrix $C_{3d}$ as a composite 3D matrix that characterizes, for a given plan, the leakage dose delivered to each voxel in the volume of interest.

D. Additional Leakage Component based on Deviation from Optimal Aperture

Figure 10:
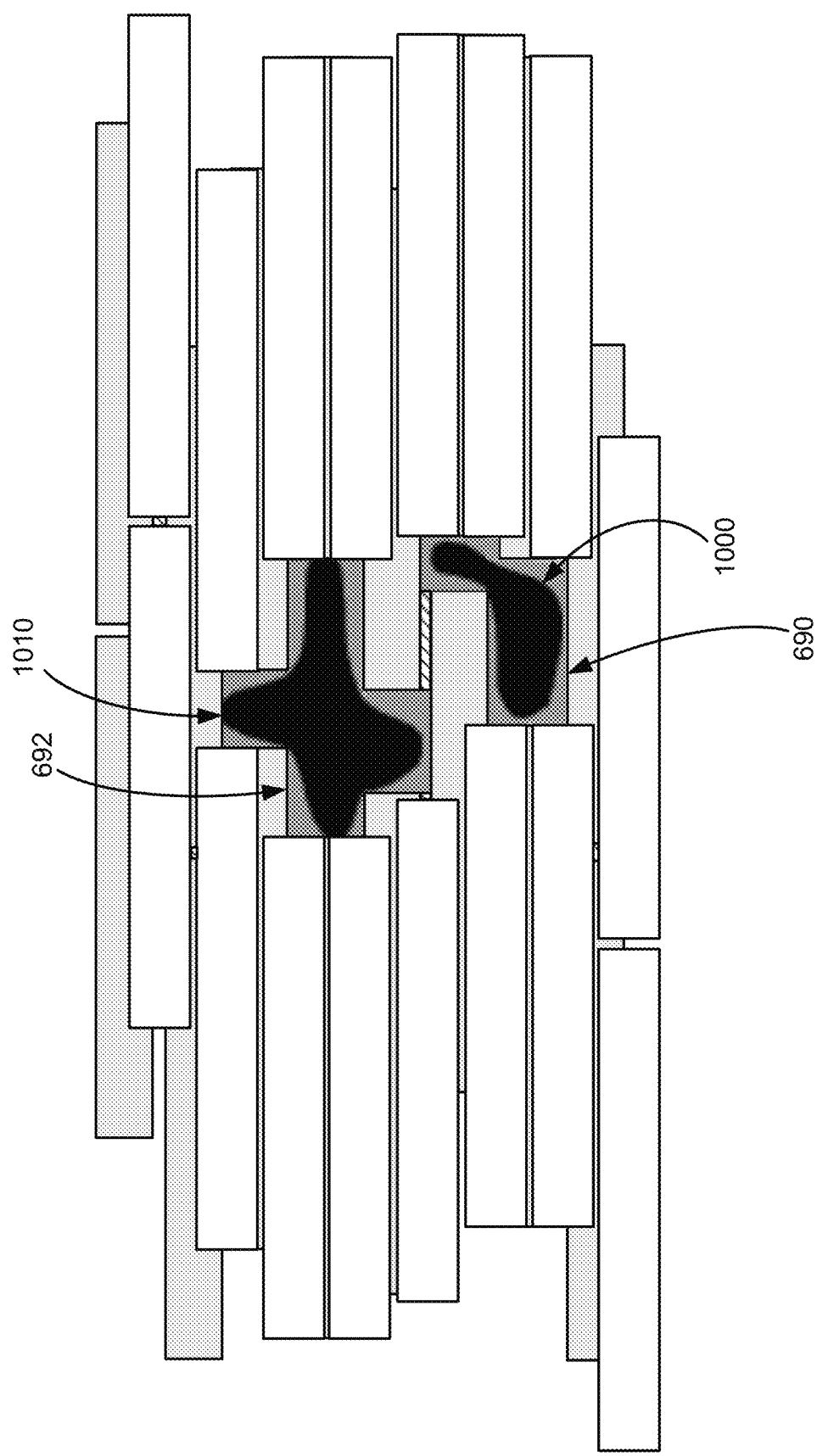
FIG. 10 shows leakage based on a difference between a target aperture and an optimal aperture.

As mentioned earlier, equation (4) can be modified to include an additional term based on a deviation from an optimal aperture. Referring to FIG. 10, an optimal aperture is shown as areas 1000 and 1010, which correspond to a sub-area within the aperture 690, 692 in FIG. 6. The optimal aperture can be calculated by the optimization engine 362 and, as shown, may include curved surfaces that cannot be replicated by the leaf structure of the MLC. That is because the geometry of the leaves, in particular the single-leaf resolution, limits the precision with which the aperture can be formed. The aperture 690, 692 is the closest possible approximation of the optimal aperture 1000, 1010, given the geometry of the leaves in FIG. 6. Areas in the aperture 690, 692 that are not contained in the optimal aperture 1000, 1010 may therefore be treated as additional leakage areas, to modify equation (4) as follows:

$$F_{2d}^i(j,k) = A_{SL}(i,j,k)R_{SL} + L_{IL}(i,j,k)r_{IL} + A_{na}(i,j,k) \tag{7}$$

where $A_{na}(i,j,k)$ is the total area of the MLC aperture (in the area of fluence pixel (j,k) of aperture i) not belonging to the optimal aperture. Additionally, $F_{2d}^i(j,k)$ can be normalized, for example, to a value between 0 and 1, where 1 corresponds to a completely open aperture.

E. Derivation of Scalar Metrics from a 3D Leakage Dose Matrix

Continuing with the method 900, in step 908, one or more scalar metrics may optionally be calculated for the 3D leakage dose matrix $C_{3d}$. The scalar metrics calculated in step 908 summarize the data values contained in the 3D leakage dose matrix $C_{3d}$, and provide a simple way of assessing the leakage delivered to the volume of interest. In one embodiment, the scalar metric can be calculated by locating the voxel which has the maximum value and outputting the maximum value as the scalar metric:

$$C_{3d}^{max} = \text{Max} C_{3d} \tag{8}$$

In another embodiment, the scalar metric can be an average value calculated by dividing a volumetric integral of the 3D leakage dose matrix $C_{3d}$ by a volumetric integral of the volume of interest V:

$$C_{3d}^{mean} = \frac{\iiint_{x \in V} C_{3d}(x) dV}{\iiint_V dV} \tag{9}$$

Another scalar metric that can derived from the 3D leakage dose matrix is the volume of the region that receives leakage radiation in the volume of interest. The volume of this leakage region can be calculated, for example, based on the total number of voxels that exceed a certain threshold.

As with the scalar metrics described in section A above, the 2D and 3D matrices (or scalar metrics derived therefrom) can be used to adjust leaf pattern settings during step 708 of method 700. For example, a threshold can be applied to each pixel position in the 2D matrix $F_{2d}^i$ or $F_{2d}^{field}$ so that one or more leaf patterns are modified when the threshold is exceeded by any pixel. Similarly, a threshold can be applied to each voxel in the 3D matrix $C_{3d}$. A less computation intensive alternative to comparing each pixel/voxel to a threshold could be to apply a threshold to a scalar metric that summarizes the information in the 2D or 3D matrix, e.g., thresholds for the metrics $C_{3d}^{max}$ and $C_{3d}^{mean}$.

When thresholds for $F_{2d}^{field}$ or $C_{3d}$ are exceeded, the entire set of leaf patterns associated with the field/plan may be excluded. Alternatively, as explained earlier in section A, leaf patterns can be modified or removed from consideration on an individual basis when a threshold for a field/plan is exceeded. For example, if the threshold for $C_{3d}$ is exceeded, the planning engine 400 can remove leaf patterns with the highest $C_{2d}$ value (e.g., removing one leaf pattern at a time) until $C_{3d}$ no longer exceeds the threshold.

V. Additional Usages of Leakage Metrics

Figure 11:
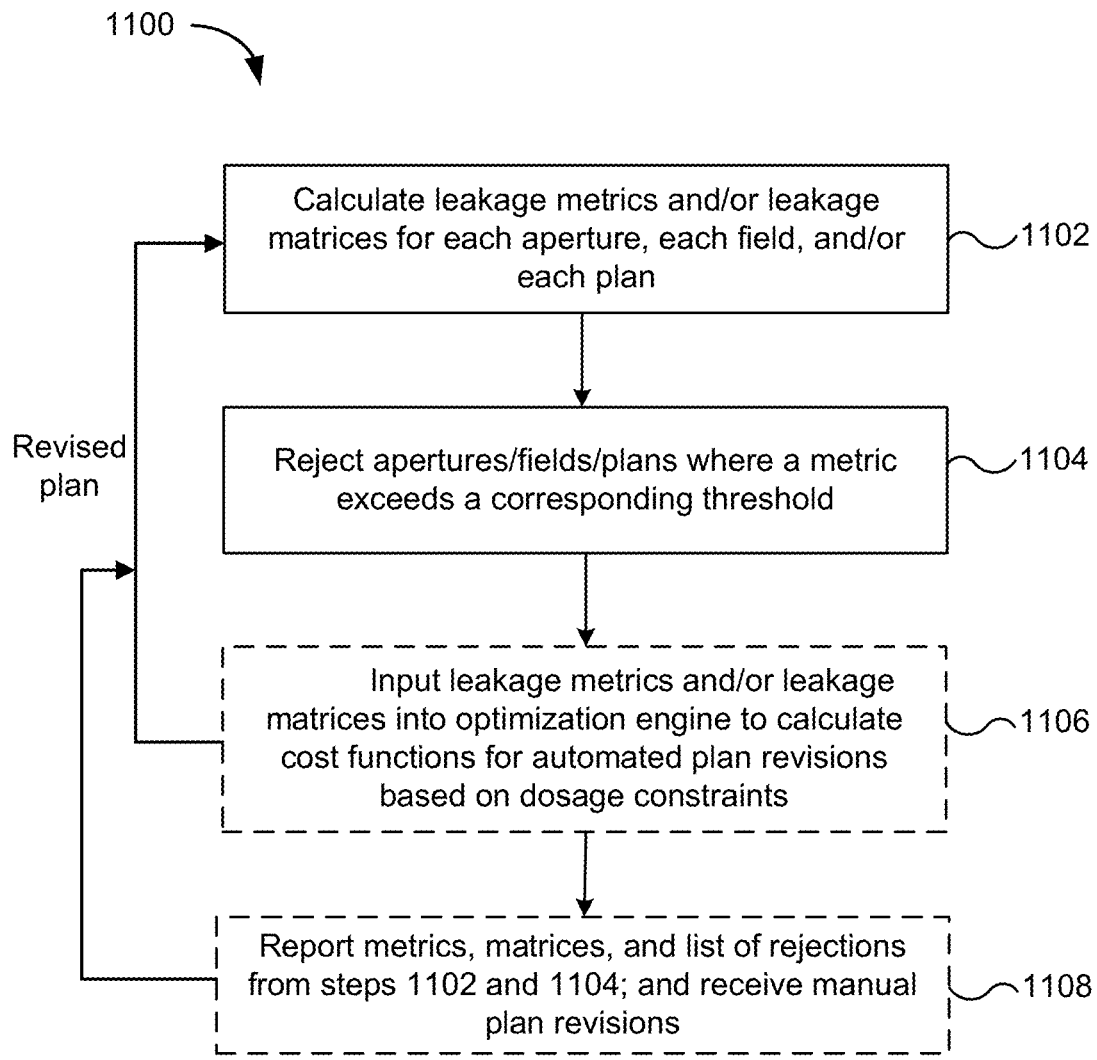
FIG. 11 is a flowchart illustrating a method for revising a treatment plan based on computed leakage metrics, according to an embodiment of the present invention.

FIG. 11 is a flowchart illustrating a method for revising a treatment plan based on computed leakage metrics, according to an embodiment of the present invention.

In step 1102, one or more of the leakage metrics and matrices described in connection with FIGS. 8 and 9 are calculated. As previously explained, the calculations can be performed for individual apertures, individual fields, or entire plans.

In step 1104, apertures, fields, or plans may be rejected if a corresponding threshold for a leakage metric is exceeded. For example, as explained earlier in section IV, the metric $C_{2d}$ may have an associated threshold that, when exceeded, causes the planning engine 400 to reject the aperture, thereby removing the leaf pattern corresponding to the aperture from being considered for inclusion in the treatment plan. Similarly, the metric $C_{2d}^{plan}$ may have a different threshold (usually higher than the threshold for $C_{2d}$) that, when exceeded, causes the planning engine 400 to reject the plan. In this manner, the planning engine 400 may apply the thresholds to automatically reject plans or plan components. The thresholds may be user configurable. Rejected apertures, fields, or plans may be revised in an attempt to qualify for acceptance, as explained below.

In step 1106, the leakage metrics and matrices may optionally be input to the optimization engine 362 in FIG. 3 in order for the optimization engine to calculate a cost function that takes the leakage metrics into consideration. Optimization techniques suitable for use with the example embodiments are described in U.S. patent application Ser. No. 14/040,468 (corresponding to U.S. Pat. No. 9,827,445) and Ser. No. 14/040,479, which are incorporated by reference herein in their entirety. The optimization engine 362 may apply a separate set of criteria to the apertures, fields, or plans from the thresholds applied by the planning engine 400 in step 1104. For example, the optimization engine 362 may factor in the leakage metrics and matrices when calculating a dose distribution for the plan and reject the plan when a dosage constraint is not met, for example, when the total dosage (including both a delivered dose and a leakage dose) exceeds a dosage limit or when the leakage dose exceeds a certain percentage of the delivered dose.

In some embodiments, the optimization engine 362 may assign a weighted penalty to an aperture, field, or plan when a dosage constraint is exceeded after factoring in the leakage metrics. The magnitude of the weighting may be in proportion to the extent to which the target volume, the non-target volume, or the entire treatment volume, receives excess radiation (e.g., the extent to which the dosage constraint is exceeded for any volume or combined volumes). If an aperture, field, or plan is rejected, the optimization engine 362 may revise the plan, for example, by adjusting the leaf settings for one or more apertures, in order to bring the plan within dosage constraints. The optimization engine 362 may also supply the revised plan to the planning engine 400 so that the revised plan is checked against the thresholds in step 1104.

In step 1108, the leakage metrics and/or leakage matrices from step 1102 and a list of apertures/fields/plans rejected in step 1104 may be reported to a user, for example output to a computer display. Plans that were accepted can be stored for optimization by the optimization engine 362 or for subsequent execution by the radiation treatment system 300. In some embodiments, the results may be displayed as a table or chart. If a 3D leakage dose matrix was calculated, the leakage dose matrix may be displayed as a 3D graphic, for example a color coded representation of the leakage dose matrix that is overlaid over an image acquired by the image acquisition system 350 or a graphical representation, of the treatment volume or target volume. The planning engine 400 may also receive manual plan revisions for leakage analysis. In some embodiments, the computer system may include a user interface through which the user can modify an aspect of a plan. For example, the user interface may permit the user to define a new leaf pattern for inclusion in the plan or modify an existing leaf pattern by repositioning a leaf. The user interface may also permit the user to remove selected leaf patterns from a particular field or plan.

VI. Computer System

Figure 12:
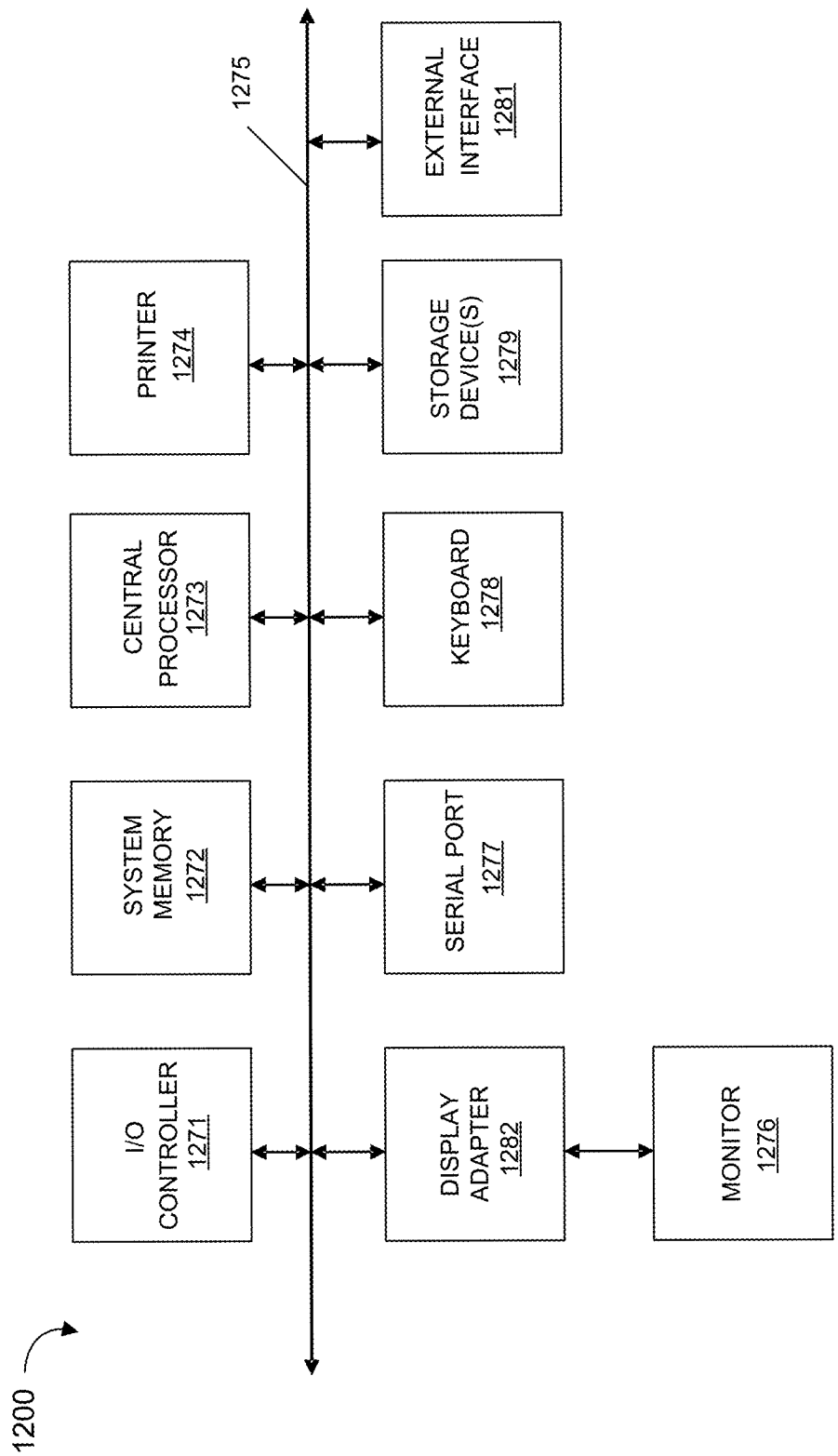
FIG. 12 shows a block diagram of an example computer system usable with a system and methods according to embodiments of the present invention.

The methods described herein may be performed by a computer system that is part of the radiation treatment system. In some embodiments, the computer system includes external components that are remotely located from the radiation system components shown in FIG. 3. The computer system can include a user interface through which the user interacts with the optimization engine 362 and the planning engine 364/400. Any of the computer systems mentioned herein may utilize any suitable number of subsystems. Examples of such subsystems are shown in FIG. 12 in a computer system 1200. In some embodiments, a computer system includes a single computer apparatus, where the subsystems can be the components of the computer apparatus. In other embodiments, a computer system can include multiple computer apparatuses, each being a subsystem, with internal components.

FIG. 12 shows a computer system 1200 including various subsystems that are interconnected via a system bus 1275. The subsystems can include a printer 1274, keyboard 1278, storage device(s) 1279, monitor 1276, which is coupled to display adapter 1282, and others shown. Peripherals and input/output (I/O) devices, which couple to I/O controller 1271, can be connected to the computer system 1200 by any number of means known in the art, such as serial port 1277. For example, serial port 1277 or external interface 1281 (e.g. Ethernet, Wi-Fi, etc.) can be used to connect computer system 1200 to a wide area network such as the Internet, a mouse input device, or a scanner. The interconnection via system bus 1275 allows the central processor 1273 to communicate with each subsystem and to control the execution of instructions from system memory 1272 or the storage device(s) 1279 (e.g., a fixed disk, such as a hard drive or optical disk), as well as the exchange of information between subsystems. The system memory 1272 and/or the storage device(s) 1279 may embody a computer readable medium. Any of the data mentioned herein can be output from one component to another component and can be output to the user.

A computer system can include a plurality of the same components or subsystems, e.g., connected together by external interface 1281 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method for determining a treatment plan for treating a patient using a radiation treatment system that includes a multi-leaf collimator (MLC), the method comprising:
   receiving, by a computer system, settings for leaf patterns of individual leaves of the MLC, each leaf pattern including a geometry of the individual leaves and forming an aperture to be used in the treatment plan;
   identifying, by the computer system, areas of radiation leakage in each of the leaf patterns, the areas of radiation leakage including first unshielded areas corresponding to gaps that are located between adjacent leaves and outside of the aperture;
   calculating, by the computer system, at least one leakage metric based on the areas of radiation leakage; and
   adjusting, by the computer system, a setting for at least one of the leaf patterns based on the at least one leakage metric.

2. The method of claim 1, further comprising:
   determining the treatment plan based on a set of leaf patterns that remain after the setting for at least one of the leaf patterns has been adjusted, the treatment plan including one or more angles of a treatment head of the radiation treatment system and a sequence of movements of the MLC, for achieving a dose distribution in a treatment volume of the patient; and
   providing, through a radiation source coupled to the treatment head, radiation at the one or more angles to specific portions of the treatment volume using the sequence of movements of the MLC according to the treatment plan.

3. The method of claim 1, wherein the treatment plan includes a plurality of radiation fields, each field corresponding to a different position of a rotating gantry of the radiation treatment system and being associated with a corresponding set of leaf patterns, the method further comprising:
   calculating, as the at least one leakage metric, a leakage metric characterizing a total leakage for all apertures formed by the set of leaf patterns associated with a particular field.

4. The method of claim 1, wherein the leaf patterns are formed by a distal leaf layer and a proximal leaf layer, and wherein the areas of radiation leakage include second unshielded areas that are shielded by only one of the distal leaf layer and the proximal leaf layer.

5. The method of claim 1, further comprising:
   calculating, by the computer system, a two-dimensional leakage matrix based on the areas of leakage, the two-dimensional leakage matrix characterizing a leakage fluence as a function of spatial position along a plane of the aperture.

6. The method of claim 5, further comprising:
   calculating, by the computer system, a three-dimensional leakage matrix by mapping the two-dimensional leakage matrix to a treatment volume in the patient, wherein the treatment volume includes a target volume intended to receive a therapeutic dose of radiation and a non-target volume intended to receive a smaller dose of radiation.

7. The method of claim 6, further comprising:
calculating, as the at least one leakage metric, a leakage metric describing a maximum value or an average value in the three-dimensional leakage matrix.

8. The method of claim 6, wherein the three-dimensional leakage matrix is mapped using a dose function by which a leakage dose is calculated for each voxel position in the treatment volume.

9. The method of claim 1, further comprising:
calculating a cost function for a treatment volume, wherein the cost function is weighted based on an extent to which the treatment volume receives excessive radiation, as determined based on the at least one leakage metric.

10. The method of claim 1, further comprising:
calculating the at least one leakage metric based on an area difference between an aperture of the leaf patterns and an optimal aperture.

11. The method of claim 1, further comprising:
calculating the at least one leakage metric as a sum of leakage values, each leakage value being associated with a unique aperture in the treatment plan.

12. The method of claim 1, further comprising:
outputting a representation of the at least one leakage metric on a display of the computer system.

13. A system including one or more processors for executing instructions stored on a computer readable medium, the computer readable medium storing instructions for controlling the one or more processors to determine a treatment plan for treating a patient using a radiation treatment system that includes a multi-leaf collimator (MLC), the instructions causing the one or more processors to:
receive settings for leaf patterns of individual leaves of the MLC, each leaf pattern including a geometry of the individual leaves and forming an aperture to be used in the treatment plan;
identify areas of radiation leakage in each of the leaf patterns, the areas of radiation leakage including first unshielded areas corresponding to gaps that are located between adjacent leaves and outside of the aperture;
calculate at least one leakage metric based on the areas of radiation leakage; and
adjust a setting for at least one of the leaf patterns based on the at least one leakage metric.

14. The system of claim 13, wherein the instructions further cause the one or more processors to:
determine the treatment plan based on a set of leaf patterns that remain after the setting for at least one of the leaf patterns has been adjusted, the treatment plan including one or more angles of a treatment head of the radiation treatment system and a sequence of movements of the MLC, for achieving a dose distribution in a treatment volume of the patient; and
cause a radiation source coupled to the treatment head to provide radiation at the one or more angles to specific portions of the treatment volume using the sequence of movements of the MLC according to the treatment plan.

15. The system of claim 13, wherein the treatment plan includes a plurality of radiation fields, each field corresponding to a different position of a rotating gantry of the radiation treatment system and being associated with a corresponding set of leaf patterns, the instructions further causing the one or more processors to:
calculate, as the at least one leakage metric, a leakage metric characterizing a total leakage for all apertures formed by the set of leaf patterns associated with a particular field.

16. The system of claim 13, wherein the leaf patterns are formed by a distal leaf layer and a proximal leaf layer, and wherein the areas of radiation leakage include second unshielded areas that are shielded by only one of the distal leaf layer and the proximal leaf layer.

17. The system of claim 13, wherein the instructions further cause the one or more processors to:
calculate a two-dimensional leakage matrix based on the areas of leakage, the two-dimensional leakage matrix characterizing a leakage fluence as a function of spatial position along a plane of the aperture.

18. The system of claim 17, wherein the instructions further cause the one or more processors to:
calculate a three-dimensional leakage matrix by mapping the two-dimensional leakage matrix to a treatment volume in the patient, wherein the treatment volume includes a target volume intended to receive a therapeutic dose of radiation and a non-target volume intended to receive a smaller dose of radiation, and wherein the three-dimensional leakage matrix is mapped using a dose function by which a leakage dose is calculated for each voxel position in the treatment volume.

19. The system of claim 18, wherein the instructions further cause the one or more processors to:
calculate, as the at least one leakage metric, a leakage metric describing a maximum value or an average value in the three-dimensional leakage matrix.

20. The system of claim 13, wherein the instructions further cause the one or more processors to:
calculate the at least one leakage metric based on an area difference between an aperture of the leaf patterns and an optimal aperture.

* * * * *